United States Patent [19]

Krämer et al.

[11] Patent Number: 4,747,869
[45] Date of Patent: May 31, 1988

[54] SUBSTITUTED AZOLYL-KETONES AND -ALCOHOLS

[75] Inventors: Wolfgang Krämer, Wuppertal; Karl H. Büchel, Burscheid; Klaus Ditgens; Hans-Ludwig Elbe, both of Wuppertal; Gerhard Jäger, Leverkusen; Manfred Jautelat, Burscheid; Klaus Lürssen, Bergisch-Gladbach; Paul Reinecke, Leverkusen, all of Fed. Rep. of Germany

[73] Assignee: Bayer Aktiengesellschaft, Leverkusen, Fed. Rep. of Germany

[21] Appl. No.: 724,375

[22] Filed: Apr. 18, 1985

Related U.S. Application Data

[63] Continuation of Ser. No. 503,220, Jun. 10, 1983, abandoned.

[30] Foreign Application Priority Data

Jun. 29, 1982 [DE]  Fed. Rep. of Germany ....... 3224129

[51] Int. Cl.$^4$ ................ C07D 249/08; A01N 43/653; A61K 31/41
[52] U.S. Cl. ...................................... 71/92; 514/383; 514/184; 548/262; 548/341
[58] Field of Search ................ 514/383, 399; 548/101, 548/262, 336, 341; 71/92, 76

[56]  References Cited

U.S. PATENT DOCUMENTS

| | | | |
|---|---|---|---|
| 4,079,143 | 3/1978 | Balasubramanyan et al. | 548/262 |
| 4,130,409 | 12/1978 | Shepard et al. | 548/262 |
| 4,243,405 | 1/1981 | Balasubramanyan et al. | 548/262 |
| 4,315,764 | 2/1982 | Reiser et al. | 71/76 |
| 4,603,140 | 7/1986 | Reiser et al. | 548/262 |

FOREIGN PATENT DOCUMENTS

| | | | |
|---|---|---|---|
| 0015639 | 9/1980 | European Pat. Off. | 262/ |
| 0016323 | 10/1980 | European Pat. Off. | 548/262 |
| 0021327 | 1/1981 | European Pat. Off. | 548/262 |
| 0031911 | 7/1981 | European Pat. Off. | 548/262 |
| 0032200 | 7/1981 | European Pat. Off. | 548/262 |
| 0079006 | 5/1983 | European Pat. Off. | 548/262 |
| 2734426 | 2/1978 | Fed. Rep. of Germany | 424/269 |
| 2805227 | 8/1978 | Fed. Rep. of Germany | 548/262 |
| 2951164 | 7/1981 | Fed. Rep. of Germany | 548/262 |
| 2951163 | 7/1981 | Fed. Rep. of Germany | 548/262 |
| 3028337 | 3/1982 | Fed. Rep. of Germany | 548/262 |

Primary Examiner—Glennon H. Hollrah
Assistant Examiner—D. L. Dinner
Attorney, Agent, or Firm—Sprung Horn Kramer & Woods

[57] ABSTRACT

Substituted azoyl-ketones and -alcohols of the formula

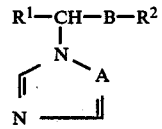

in which
 A is a nitrogen atom or the CH group,
 B is CO or CH(OH),
 $R^1$ is alkyl, alkenyl, alkinyl, optionally substituted phenylalkyl, optionally substituted cycloalkyl or optionally substituted cycloalkylalkyl,
 $R^2$ is optionally substituted cycloalkyl or the grouping —C(CH$_3$)$_2$R$^3$, and
 $R^3$ is alkyl having more than 2 carbon atoms, alkenyl, alkinyl or the —CH=O group or a derivative thereof, or addition products thereof with acids or metal salts, exhibit plant growth regulating and fungicidal properties, several intermediates therefor are new.

8 Claims, No Drawings

SUBSTITUTED AZOLYL-KETONES AND -ALCOHOLS

This is a continuation of application Ser. No. 503,220, filed June 10, 1983, now abandoned.

The present invention relates to new substituted azolyl-ketones and -alcohols, several processes for their preparation and their use as fungicides and plant growth regulators.

It has already been disclosed that certain azolyl-pentanones; such as, for example, 1-(4-chlorophenyl)-4,4-dimethyl-2-(1,2,4-triazol-1-yl)-pentan-3-one, possess good fungicidal properties (see DE-OS (German Published Specification) No. 2,734,426). Furthermore, it has been disclosed that cartain azolyl-butanones and -ols, such as, for example, alkylated 3,3-dimethyl-4-fluoro(-chloro)-1-(1,2,4-triazol-1-yl)-butan-2-ones and -ols, have good fungicidal and plant growth-regulating properties (see DE-OS (German Published Specification) No. 2,951,164 and DE-OS (German Published Specification) No. 2,951,163).

However, the action of all these compounds in certain fields of indication is not always completely satisfactory, particularly when low amounts and concentrations are used.

New substituted azolyl-ketones and -alcohols of the general formula

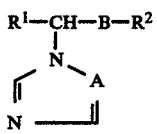     (I)

in which
A represents a nitrogen atom or the CH group,
B represents the keto or CH(OH) group,
$R^1$ represents alkyl, alkenyl, alkinyl, optionally substituted phenylalkyl, optionally substituted cycloalkyl or optionally substituted cycloalkylalkyl, and
$R^2$ represents optionally substituted cycloalkyl or the grouping $—C(CH_3)_2R^3$,
wherein
$R^3$ represents alkyl having more than 2 carbon atoms, alkenyl, alkinyl and the $—CH=O$ group and its derivatives,
and their acid addition salts and metal salt complexes have been found.

Those compounds of the formula (I) in which B represents a CH(OH) group possess two asymmetric carbon atoms: they can therefore occur as the two geometric isomers (erythro and threo form), which may be obtained in varying proportions. In all cases, they are present as enantiomer pairs.

Furthermore, it has been found that the new substituted azolyl-ketones and -alcohols of the formula (I) are obtained when (a) azolyl-ketones of the formula

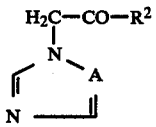     (II)

in which

A and $R^2$ have the meaning given above, are reacted with an alkylating agent of the formula $R^1—Z$     (III)

in which
$R^1$ has the meaning given above and
Z represents an electron-attracting leaving grouping,
in the presence of a base and in the presence of an organic diluent, or in an aqueous-organic two-phase system in the presence of a phase-transfer catalyst; or (b) halogenoketones of the formula

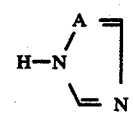     (IV)

in which
$R^1$ and $R^2$ have the meaning given above and
Hal represents halogen, in particular chlorine or bromine,
are reacted with azoles of the formula

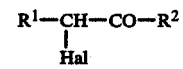     (V)

in which
A has the meaning given above, in the presence of a diluent and in the presence of an acid-binding agent: and, if aopropriate, (c) the compounds obtained by processes (a) and (b), of the formula

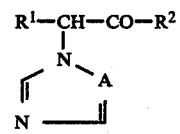     (Ia)

in which
A, $R^1$ and $R^2$ have the meaning given above, are reduced in a customary manner, according to known methods.

The resulting compounds of the formula (I) can, if desired, then be subjected to an addition reaction with an acid or a metal salt. In some cases, it proves advantageous to obtain the compounds of the formula (I) in pure form via their salts.

Furthermore, it has been found that the new substituted azolyl-ketones and -carbinols of the formula (I) have powerful fungicidal and plant growth-regulating properties. In this context, the compounds according to the invention, of the formula (I), surprisingly show better fungicidal and better plant growth-regulating actions than the abovementioned triazolylalkanones and -ols, which are known from the prior art and are similar compounds chemically and in terms of their action. The active compounds according to the invention thus represent an enrichment of the art.

Furthermore, the new substituted azolylketones and -carbinols of the formula (I) are interesting intermediate products. Thus, by appropriate reactions, it is possible to obtain functional derivatives of the keto group, such as, for example, oximes and oxime-ethers, hydrazones and ketals. Furthermore, the compounds of the formula (I) can be converted at the hydroxyl group in a customary manner to give the corresponding ethers; or acyl or carbamoyl derivatives of the compounds of the formula (I) can be obtained by reaction with, for example, acyl halides or carbamoyl chlorides, in a manner which is known in principle.

Formula (I) gives a general definition of the substituted azolyl-ketones and -alcohols according to the invention. In this formula:

$R^1$ preferably represents straight-chain or branched alkyl having 1 to 12 carbon atoms, straight-chain or branched alkenyl and alkinyl, each having 2 to 12 carbon atoms, or phenylalkyl which has 1 to 4 carbon atoms in the alkyl part and is optionally monosubstituted to trisubstituted by identical or different substituents, the following being mentioned as phenyl substituents: halogen, alkyl, alkoxy and alkylthio, each having 1 to 4 carbon atoms; or preferably represents cyclohexyl; dialkylamino having 1 to 4 carbon atoms in each alkyl part; halogenoalkyl, halogenoalkoxy and halogenoalkylthio; each having 1 to 4 carbon atoms and 1 to 5 identical or different halogen atoms, such as fluorine atoms and chlorine atoms, nitro and cyano; alkoxycarbonyl having 1 to 4 carbon atoms in the alkyl part; and optionally halogen-substituted phenyl and phenoxy; and also cycloalkyl and cycloalkylalkyl, each of which has 3 to 7 carbon atoms in the cycloalkyl part and 1 to 4 carbon atoms in the alkyl part and is optionally monosubstituted to trisubstituted by identical or different alkyl radicals having 1 to 4 carbon atoms; $R^2$ preferably represents cycloalkyl which has 3 to 7 carbon atoms and is optionally monosubstituted to trisubstituted by identical or different alkyl radicals having 1 to 4 carbon atoms; and the grouping $-C(CH_3)_2R^3$, wherein $R^3$ preferably represents straight-chain or branched alkyl having 3 to 6 carbon atoms, straight-chain or branched alkenyl having 2 to 4 carbon atoms, alkinyl having 3 to 5 carbon atoms or the $-CH=O$ group and its derivatives, such as oximes, oximeethers and acetals, for example alkoxyiminomethyl having 1 to 4 carbon atoms in the alkyl part, dialkoxymethyl having 1 to 4 carbon atoms in each alkyl part and optionally substituted dioxolanes and dioxanes, and A and B preferably have the meanings given in the definition of the invention.

Particularly preferred compounds of the formula (I) are those
in which
$R^1$ represents straight-chain or branched alkyl having 1 to 6 carbon atoms, straight-chain or branched alkenyl and alkinyl, each having 2 to 6 carbon atoms, and phenylalkyl which has 1 to 2 carbon atoms in the alkyl part and is optionally monosubstituted or disubstituted by identical or different substituents, the following being mentioned as phenyl substituents: fluorine, chlorine, methyl, ethyl, isopropyl, tert.-butyl, methoxy, methylthio, cyclohexyl, dimethylamino, trifluoromethyl, trifluoromethoxy, trifluoromethylthio, nitro, cyano, methoxycarbonyl, or phenyl and phenoxy, each of which is optionally substituted by chlorine and fluorine; and also represents cyclopropyl, cyclopropylmethyl, cyclopentyl, cyclopentylmethyl, cyclohexyl, cyclohexylmethyl and cycloheptyl, each of which is optionally monosubstituted or disubstituted by identical or different substituents from amongst methyl, ethyl, isopropyl and tert.-butyl;

$R^2$ represents cyclopropyl, cyclopentyl and cyclohexyl, each of which is optionally monosubstituted or disubstituted by identical or different substituents from amongst methyl, ethyl, isopropyl and tert.-butyl, and represents the grouping $-(CH_3)_2R^3$, wherein $R^3$ represents straight-chain or branched alkyl having 3 to 6 carbon atoms, vinyl, propargyl or the $-CH=O$ group, methoxyiminomethyl, dimethoxymethyl, or the dioxolane and 1,3-dioxane radicals; and A and B have the meaning given in the definition of the invention.

Preferred compounds according to the invention are also addition products of acids and those substituted azolyl-ketones and -alcohols of the formula (I) in which the substituents A, B, $R^1$ and $R^2$ have the meanings which have already been mentioned as being preferred for these substituents.

The acids with which addition products can be formed preferably include hydrohalic acids, such as, for example, hydrochloric acid and hydrobromic acid, in particular hydrochloric acid, and also phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, salicylic acid, sorbic acid and lactic acid, as well as sulphonic acids, such as, for example, p-toluenesulphonic acid and naphthalene-1,5-disulphonic acid.

Further preferred compounds according to the invention are addition products of salts of metals of main groups II to IV and of sub-groups I and II and IV to VIII and those substituted azolyl-ketones and -alcohols of the formula (I) in which the substituents Ar, B and $R^1$ have the meanings which have already been mentioned as being preferred for these radicals. In this context, salts of copper, zinc, manganese, magnesium, tin, iron and nickel are particularly preferred. Suitable anions of these salts are those which are derived from those acids which lead to physiologically tolerated addition products. Particularly preferred acids of this type in this connection are the hydrohalic acids, such as, for example, hydrochloric acid and hydrobromic acid, and also phosphoric acid, nitric acid and sulphuric acid.

If, for example, 3-(dioxolan-2-yl)-3-methyl-1-(1,2,4-triazol-1-yl)-butan-2-one and 2,4-dichlorobenzyl bromide are used as starting materials, the course of the reaction can be represented by the following equation (process a):

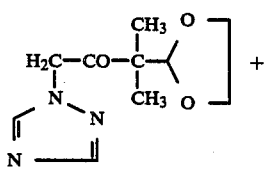

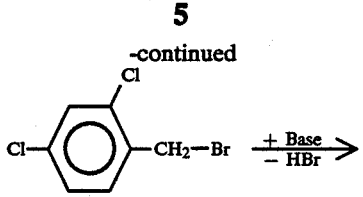

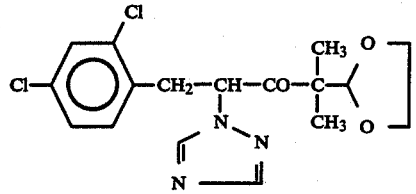

It, for example, 4-bromo-2-(dioxolan-2-yl)-5-(2,4-dichlorophenyl)-2-methyl-pentan-3-one and 1,2,4-triazole are used as starting materials, the course of the reaction can be represented by the following equation (process b):

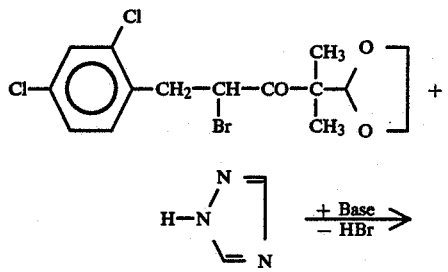

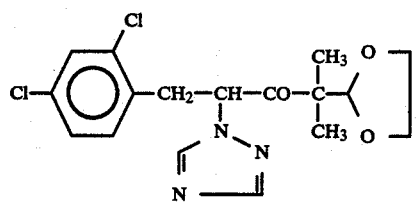

If, for example, 1-(2,4-dichlorophenyl)-4-(dioxolan-2-yl)-4-methyl-2-(1,2,4-triazol-1-yl)-pentan-3-one and sodium borohydride are used as starting materials, the course of the reaction can be represented by the following equation (process c):

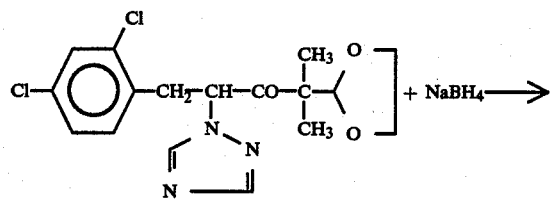

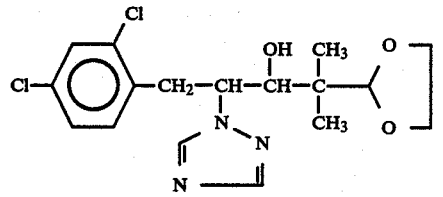

Formula (II) gives a general definition of the azolyl-ketones to be used as starting materials in carrying out process (a) according to the invention. In this formula, A and R² preferably represent the radicals which have already been mentioned in connection with the description of the substances according to the invention, of the formula (I), as being preferred for these substituents.

Some of the azolyl-ketones of the formula (II) are known (see, for example, U.S. application Ser. No. 792,756, filed May 2, 1977, pending and DE-OS (German Published Specification) No. 3,028,330); some of them form the subject of prior patent application which have not yet been published (see the German Patent Applications Nos. P 31 45 857 of Nov. 19, 1981, P 31 45 858 of Nov. 19, 1981 and P 32 09 431 of Mar. 16, 1982; they are obtained for example, by reacting the corresponding halogenoketones with imidazole or 1,2,4-triazole. Azolyl-ketones of the general formula

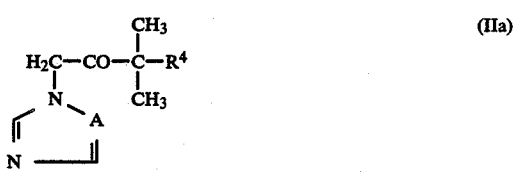

in which

A has the meaning given above and

R⁴ represents the —CH=O group and its derivatives, are hitherto unknown.

The new azolyl-ketones of the formula (IIa) are generally interesting intermediate products, and can be obtained by reacting halogenomethyl-ketones of the formula

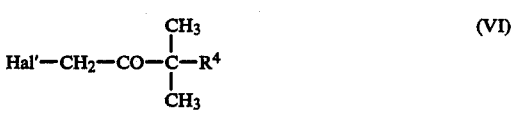

in which

Hal' represents chlorine or bromine and

R⁴ has the meaning given above, in a customary manner with 1,2,4-triazole or imidazole, in the presence of an inert organic solvent, such as, for example, acetone, and in the presence of an acid-binding agent, such as, for example, potassium carbonate, at temperatures between 20° and 150° C.

The halogenomethyl-ketones of the formula (VI) likewise are hitherto unknown. They are obtained when 1-(N-morpholino)-isobutene of the formula

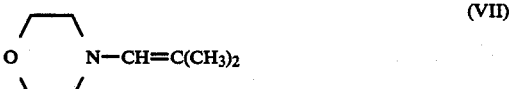

is reacted with halogenoacetyl chlorides of the formula

in which

Hal' has the meaning given above, in the presence of a solvent, such as, for example, diethyl ether, at temperatures between 20° and 120° C., and, if appropriate, the resulting halogenomethylketones of the formula

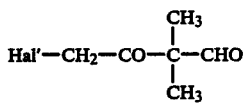

(VIa)

in which
Hal' has the meaning given above, are derivatised at the aldehyde group in a customary manner, such as, for example, by reaction with diols in the presence of an inert organic solvent, such as, for example, toluene, and in the presence of a strong acid as a catalyst, such as, for example, p-toluenesulphonic acid, at temperatures between 80° and 100° C.

Formula (III) gives a general definition of the alkylating agents additionally to be used as starting materials for process (a) according to the invention. In this formula, $R^1$ preferably represents those radicals which have already been mentioned in connection with the description of the substances according to the invention, of the formula (I), as being preferred for these substituents. Z preferably represents an electron-attracting leaving grouping, such as, for example, halogen, p-methylphenylsulphonyloxy, the grouping —O—SO$_2$—OR or —NR$_3$ and others (in these formulae, R represents, for example, alkyl having 1 to 4 carbon atoms).

The alkylating agents of the formula (III) are generally known compounds.

Formula (IV) gives a general definition of the halogenoketones to be used as starting materials in carrying out process (b) according to the invention. In this formula, $R^1$ and $R^2$ preferably represent the radicals which have already been mentioned in connection with the description of the substances according to the invention, of the formula (I), as being preferred for these substituents.

The halogenoketones of the formula (IV) are hitherto unknownn; however, they can be obtained in a generally known manner, by reacting, for example, the corresponding ketones with chlorine or bromine in the presence of an inert organic solvent, such as, for example, chlorinated hydrocarbons, at room temperature, or with customary chlorinating agents, such as, for example, sulphuryl chloride, at temperatures between 20° and 60° C.

Formula (V) gives a general definition of the azoles additionally to be used as starting materials for process (b) according to the invention. In this formula, A preferably has the meanings given in the definition of the invention.

The azoles of the formula (V) are generally known compounds.

Formula (Ia) gives a general definition of the compounds to be used as startig materials in carrying out process (c) according to the invention. The compounds of the formula (Ia) are substances according to the invention.

Suitable diluents for process (a) according to the invention are inert organic solvents. These preferably include aromatic hydrocarbons, such as benzene, toluene or xylene; halogenated hydrocarbons, such as methylene chloride, carbon tetrachloride, chloroform or chlorobenzene; esters, such as ethyl acetate: formamides, such as dimethylformamide; and dimethylsulphoxide.

Process (a) according to the invention is carried out in the presence of a base. All customary organic and, in particular, inorganic bases, such as, preferably, alkali metal hydroxides or alkali metal carbonates, can be employed for this process, and sodium hydroxide and potassium hydroxide may be mentioned as examples.

In carrying out process (a) according to the invention, the reaction temperatures can be varied within a relatively wide range. In general, the reaction is carried out at between 0° and 100° C., preferably between 20° and 100° C.

In carrying out process (a) according to the invention, equimolar amounts are preferably employed. The end products of the formula (I) are isolated in a generally customary manner.

Process (a) according to the invention can also be carried out in a two-phase system, such as, for example, aqueous sodium hydroxide or potassium hydroxide solution/toluene or methylene chloride, if appropriate with the addition of 0.1 to 1 mol of a phase-transfer catalyst, such as, for example, ammonium or phosphonium compounds, benzyldodecyl-dimethyl-ammonium chloride and triethyl-benzyl-ammonium chloride being mentioned as examples.

Suitable diluents for process (b) according to the invention are inert organic solvents. These preferably include ketones, such as diethyl ketone and, in particular, acetone and methyl ethyl ketone; nitriles, such as propionitrile, and in particular acetonitrile; alcohols, such as ethanol or isopropanol; ethers, such as tetrahydrofuran or dioxane; aromatic hydrocarbons, such as toluene, benzene or chlorobenzene; formamides, such as, in particular, dimethylformamide; and halogenated hydrocarbons.

Process (b) according to the invention is carried out in the presence of an acid-binding agent. It is possible to add all customarily usable inorganic and organic acid-binding agents, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine, N,N-dimethylbenzylamine, and furthermore pyridine and diazabicyclooctane. Preferably, an appropriate excess of azole is used.

In process (b) according to the invention, the reaction temperatures can be varied within a relatively wide range. In general, the reaction is carried out at between about 20° and about 150° C., preferably at 40° to 100° C. When a solvent is present, the reaction is advantageously carried out at the boiling point of the particular solvent.

In carrying out process (b) according to the invention, 2 to 4 mols of azole and 1 to 4 mols of the acid-binding agent are preferably employed per mol of the compounds of the formula (IV). To isolate the compounds of the formula (I), the solvent is distilled off and the residue is worked up in the customary manner.

The reduction according to the invention by process (c) is carried out in a customary manner, for example by reaction with complex hydrides, if appropriate in the presence of a diluent, or by reaction with aluminum isopropylate in the presence of a diluent.

If complex hydrides are employed, suitable diluents for the reaction according to the invention are polar organic solvents. These preferably include alcohols, such as methanol, ethanol, butanol or isopropanol, and ethers, such as diethyl ether or tetrahydrofuran. The reaction is carried out in general at 0° to 30° C., preferably at 0° to 20° C. For this purpose, about 1 mol of a complex hydride, such as sodium borohydride or lithium alanate, is employed per mol of the ketone of the formula (I). To isolate the reduced compounds of the formula (I), the residue is taken up in dilute hydrochloric acid, and the solution is then rendered alkaline, and extracted with an organic solvent. Further working-up is effected in the customary manner.

If aluminum isopropylate is employed, preferred diluents for the reaction according to the invention are alcohols, such as isopropanol, or inert hydrocarbons, such as benzene. The reaction temperatures once again can be varied within a relatively wide range; in general, the reaction is carried out at between 20° and 120° C., preferably at 50° to 100° C. To carry out the reaction, about 0.3 to 2 mols of aluminum isopropylate are employed per mol of the ketone of the formula (I). To isolate the reduced compounds of the formula (I), the excess solvent is removed in vacuo, and the aluminum compounds formed are decomposed with dilute sulphuric acid or sodium hydroxide solution. Further working-up is effected in the customary manner.

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoted vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus, it is possible, for example, to increase the content of sugar in sugar beet, sugar cane, pineapples and citrus fruit or to increase the protein content in soy beans or cereals. Using growth-regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance, there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for exampe, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants of frost, drought or a high salt content in the soil can be induced with growth regulators. Cultivations of plants in regions which are usually unsuitable for this purpose thereby becomes possible.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae,, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases; thus, for combating Erysiphe species, such as, for example, against the powdery mildew of barley or cereals causative organism (*Erysiphe graminis*), or Sphaerotheca species, such as, for example, against the powdery mildew of cucumber causative organism (*Sphaerotheca fuligenea*); and also for combating further cereal diseases, such as *Cochliobolus sativus* and *Pyrenophora teres*, and rice diseases, such as *Pyricularia oryzae* and *Pellicularia sasakii*. The additional bactericidal action should be singled out.

The active compounds can be converted to the customary formulations, such as solutions, emulsions, suspensions, powders, foams, pastes, granules; aerosols, very fine capsules in polymeric substances and in coating compositions for seed, as well as ULV formulations.

These formulations are produced in known manner, for example by mixing the active compounds with extenders, that is, liquid solvents, liquefid gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers; alkylsulphonates, alkyl-sulphates, arylsulphonates as well as albumin hydrolysation products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulation as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsion foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are employed as plant growth regulators, the amounts applied can be varied within a substantial range. In general, 0.01 to 50 kg, preferably 0.05 to 10 kg, of the active compound are employed per hectare of soil surface.

When the substances according to the invention are employed as plant growth regulators, the rule is that they are applied within a preferred period of time, the exact definition of which depends on the climatic and vegetative circumstances.

When the substances according to the invention are employed as fungicides, also, the amount employed can be varied within a substantial range, depending on the type of application. Thus, in the treatment of parts of plants, the active compound concentrations in the use forms are in general between 1 and 0.0001% by weight, preferably between 0.5 and 0.001%. In the treatment of seed, amounts of active compound of 0.001 to 50 g per kilogram of seed, preferably 0.01 to 10 g, are generally required. In the treatment of soil, active compound concentrations of 0.00001 to 0.1% by weight, preferably 0.0001 to 0.02%, are required at the place of action.

PREPARATION EXAMPLES

Example 1

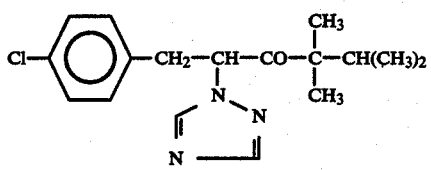

(Process a)

15.6 g (0.08 mol) of 1-(1,2,4-triazol-1-yl)-3,3,4-trimethylpentan-2-one are dissolved in 100 ml of dimethylsulphoxide, and 4.5 g (0.08 mol) of potassium hydroxide, dissolved in 10 ml of water, are added, while cooling. 16.4 g (0.08 mol) of 4-chlorobenzyl bromide, dissolved in 50 ml of dimethylsulphoxide, are added dropwise to the mixture at a rate such that the temperature does not exceed 40° C. Thereafter, the mixture is slowly warmed to 100° C. and stirred for a further 15 hours at this temperature, and the cooled solution is poured onto 500 ml of water. The mixture is extracted with twice 250 ml of methylene chloride, the methylene chloride phase is then extracted with four times 100 ml of water, and the organic phase is evaporated down. The residue is taken up in 100 ml of acetone, and 14.4 g of naphthalene-1,5-disulphonic acid, dissolved in 50 ml of acetone, are added. The 2,3,3-trimethyl-5-(1,2,4-triazol-1-yl)-6-(4-chlorophenyl)-hexan-3-one salt of naphthalene-1,5-disulphonic acid crystallizes out. The precipitate is filtered off under suction and taken up in 250 ml of saturated sodium bicarbonate solution, the aqueous phase is extracted with four times 100 ml of methylene chloride, the methylene chloride phase is extracted with 100 ml of water, and the solvent is distilled off from the organic phase. 17.3 g (67.6% of theory) of 2,3,3-trimethyl-5-(1,2,4-triazol-1-yl)-6-(4-chlorophenyl)-hexan-4-one are obtained as colorless crystals of melting point 91°-94° C.

Preparation of the starting material

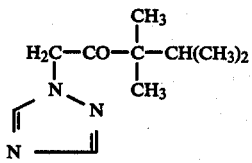

162.5 g (1 mol) of 1-chloro-3,3,4-trimethylpentan-2-one are added dropwise to a suspension of 84 g (1.2 mols) of 1,2,4-triazole and 165.6 g (1.2 mols) of potassium carbonate in 1 liter of ethanol. The mixture is stirred for 15 hours at 40° C., the inorganic precipitate is filtered off under suction, the solvent is distilled off, the precipitate is taken up in 500 ml of methylene chloride, the organic phase is extracted with 1 liter of water, the aqueous phase is extracted with 500 ml of methylene chloride, the methylene chloride phases are combined, and the combined phases are extracted with twice 1 liter of water. The solvent is distilled off from the organic phase. 154.6 g (79.3% of theory) of 1-(1,2,4-triazol-1-yl)-3,3,4-trimethylpentan-2-one are obtained as a colorless oil of refractive index $n_D^{20}=1.4827$.

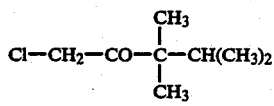

238 g (1 mol) of 1-chloro-2-phenoxy-3,3,4-trimethylpent-1-ene are stirred with 500 g of formic acid and 50 g of concentrated hydrochloric acid for 2 hours at 80° C. The mixture is diluted with methylene chloride, and is washed once with water and four times with dilute sodium hydroxide solution. After the mixture has been dried over sodium sulphate, the solvent is stripped off in vacuo, and the residue is distilled over a column. 125 to 135 g (77–83% of theory) of 1-chloro-3,3,4-trimethylpentan-2-one of boiling point 88°–93° C./16 mbar are obtained.

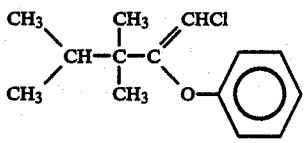

487 g of sodium phenolate are introduced into 1.6 liters of N-methylpyrrolidone at about 100° C., and dissolved by heating the mixture to 200° C. 360 g (2 mols) of 1,1-dichloro-3,3,4-trimethyl-pent-1-ene are added dropwise in the course of 3 hours at a rate such that the temperature of the reaction mixture does not fall below 195° C. Thereafter, the mixture is heated at 200°–210° C. for 8 hours. Working-up is carried out by diluting the solution with methylene chloride and extracting it by shaking withh dilute sodium hydroxide solution. After drying and stripping off the solvent, 406 g of crude product remain, this product being distilled at 105°–120° C./0.1 mbar. 337 g (71% of theory) of 1-chloro-2-phenoxy-3,3,4-trimethyl-pent-1-ene are obtained.

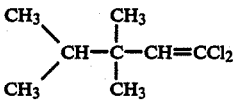

20 g of anhydrous, powdered aluminum chloride are added in portions to 2,040 g (21 mols) of vinylidene chloride at −10° C., in a dry apparatus equipped with a drying tube. 837 g (7 mols) of 2-chloro-2,3-dimethylbutane are then added dropwise in the temperature range from 0° to 10° C. The mixture is allowed to warm up to 20° C., and further aluminum chloride portions (a maximum of 20 g) are added, while cooling, until the reaction is no longer exothermic. The mixture is stirred for a further 4 hours at room temperature, the catalyst is deactivated by dropwise addition of 70 ml of acetic acid, and the mixture is filtered over sodium sulphate. The volatile constituents are separated from the sparingly volatile constituents by continuous-feed distillation under 1 mbar. The distillate is fractionated in a column. 824 g (65% of theory) of 1,1-dichloro-3,3,4- trimethyl-pent-1-ene of boiling point 60°–75° C./20 mbar are obtained.

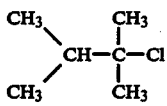

About 440 g (12 mols) of hydrogen chloride from a cylinder are passed, in the course of 16 hours, into 840 g (10 mols) of 2,3-dimethyl-but-1-ene at 10° to 20° C., while cooling with ice. According to IR, conversion is then complete. Excess hydrogen chloride is drawn off with a water jet pump. 1,103 g (91% of theory) of 2-chloro-2,3-dimethyl-butane are obtained.

EXAMPLE 2

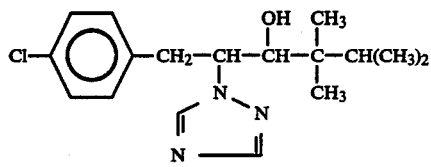

(Process c)

13.8 g (0.043 mol) of 2,3,3-trimethyl-5-(1,2,4-triazol-1-yl)-6-(4-chlorophenyl)-hexan-4-one (Example 1) are dissolved in 100 ml of methol, and 2.1 g (0.056 mol) of sodium borohydride are added in portions at 0° to 10° C., the mixture is then allowed to react for a further 15 hours at room temperature, 90 ml of 2N hydrochloric acid are added dropwise, and stirring is continued for a further 15 hours at room temperature.

300 ml of saturated sodium bicarbonate solution are added, the mixture is extracted with twice 250 ml of methylene chloride, and washed with 250 ml of methylene chloride in each case, the methylene chloride phase is washed with three times 50 ml of water, and the methylene chloride is distilled off. 10 g (72.5% of theory) of 2,3,3-trimethyl-5-(1,2,4-triazol-1-yl)-6-(4-chlorophenyl)-hexan-4-ol are obtained as colorless crystals of melting point 106°–08° C.

EXAMPLE 3

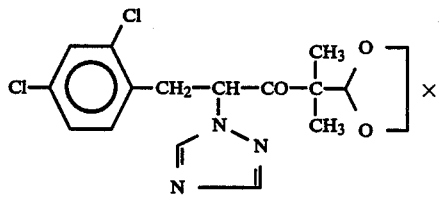

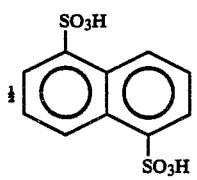

(Process a)

34 g (0.15 mol) of 1-(1,2,4-triazol-1-yl)-3-(dioxolan-2-yl)-3-methyl-butan-2-one in 150 ml of dimethylsulphoxide are initially introduced, 8.4 g of powdered potassium hydroxide are added at 15° C., and 36 g (0.15 mol) of 2,4-dichlorobenzyl bromide, dissolved in 30 ml of dimethylsulphoxide, are added dropwise. The reaction mixture is stirred for a further 15 hours at 20° C., and the suspension is poured onto 500 ml of water. The mixture is extracted with 600 ml of methylene chloride, the organic phase is washed with twice 1 liter of water, and the solvent is distilled off. The oily residue is dissolved in 600 ml of acetone, and naphthalene-1,5-disulphonic acid in 60 ml of acetone is added. At 0° C., crystallization occurs after 6 hours. 50 g of (38.6% of theory) of 1-(2,4-dichlorophenyl)-2-(1,2,4-triazol-1-yl)-4-(dioxolan-2-yl)-4-methyl-pentan-3-one naphthalene-1,5-disulphonate of melting point 199°–201° C. are obtained.

Preparation of the starting material

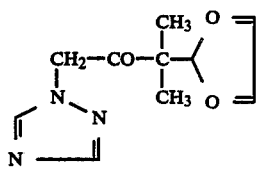

180.6 g (0.94 mol) of 1-chloro-3-(dioxolan-2-yl)-3-methyl-butan-2-one, 64.9 g (0.94 mol) of 1,2,4-triazole and 142.7 g (1 mol) of potassium carbonate in 1,000 ml of methyl ethyl ketone are heated under reflux for 16 hours. The solid is filtered off under suction and the solvent is distilled off, the oily residue is taken up in 700 ml of methylene chloride, and the organic phase is extracted with twice 1,000 ml of water. The solvent is distilled off from the organic phase. 151.3 g (71.5% of theory) of 1-(1,2,4-triazol-1-yl)-3-(dioxolan-2-yl)-3-methyl-butan-2-one are obtained as an oil with a purity of 99% according to gas chromatography.

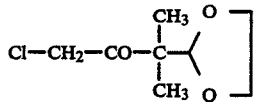

204 g (1.38 mol) of 2,2-dimethyl-4-chloro-3-ketobutanal are heated with 93 g (1.5 mols) of ethylene glycol and 0.7 g of p-toluenesulphonic acid in 400 ml of methylene chloride for 3 hours in a water separator. The organic phase is extracted with 150 ml of 5% strength sodium hydroxide solution, and thereafter with 400 ml of water. The solvent is distilled off and the residue is distilled under the vacuum from a water jet. 211 g (79.8% of theory) of 1-chloro-3-(dioxolan-2-yl)-3-methylbutan-2-one of boiling point 127°–28° C./14 mbar are obtained.

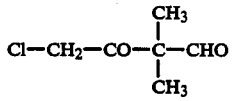

210 g (1.5 mols) of 1-morpholino-2-methyl-prop-1-ene are added dropwise, in the course of one hour, to 169.0 g (1.5 mols) of chloroacetyl chloride, dissolved in 350 ml of diethyl ether, at 5° C. After the addition is complete, the mixture is stirred for a further 3 hours under reflux. The solution is poured onto 100 g of ice and brought to pH 5 with aqueous sodium bicarbonate solution, and the ether phase is separated off. The aqueous phase is extracted with 100 ml of diethyl ether, the organic phases are combined, and dried over sodium sulphate, the solvent is distilled off and the residue is distilled under the vacuum from a water jet. 136.4 g (61% of theory) of 4-chloro-3-keto-2,2-dimethylbutanal of boiling point 95°–98° C./14 mbar are obtained.

Examples 4 and 5

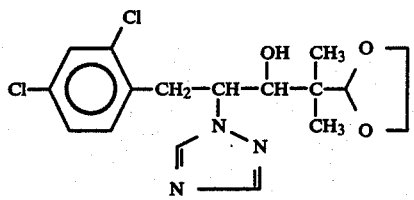

Example 4: B form*
Example 5: A form*
*A and B forms: the two possible geometric isomers (Process c)

22.9 g (0.06 mol) of 1-(2,4-dichlorophenyl)-2-(1,2,4-triazol-1-yl)-4-(dioxolan-2-yl)-4-methyl-pentan-3-one are dissolved in 100 ml of methanol, the solution is cooled to 0° C., and 2.95 g (0.078 mol) of sodium borohydride are added in portions. The mixture is stirred for a further 3 hours at room temperature, 15 ml of concentrated hydrochloric acid are added dropwise, stirring is continued for a further 3 hours and 500 ml of saturated sodium bicarbonate solution are then added. The mixture is extracted with 400 ml of methylene chloride, the phases are separated, the organic phase is wshed with twice 100 ml of water, and the solvent is distilled off. The residue is taken up in 150 ml of diisopropyl ether, and the crystals are filtered off under suction. 1-(2,4-Dichlorophenyl)-2-(1,2,4-triazol-1-yl)-4-(dioxolan-2-yl)-4-methyl-pentan-3-ol is obtained as the B form of melting point 178°–81° C., and after approximately 100 ml of diisopropyl ether have been distilled off, 8.9 g of product are obtained as the A form of melting point 95°–100° C.

Example 6

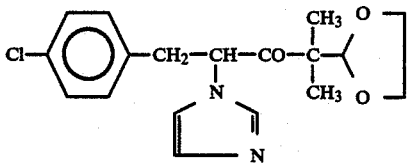

(Process a)

30 g (0.131 mol) of 1-(imidazol-1-yl)-3-(dioxolan-2-yl)-3-methyl-butan-2-one are dissolved in 130 ml of dimethylsulphoxide, 7.5 g of powdered potassium hydroxide are added at 10° C., and 21 g of 4-chlorobenzyl chloride (0.131 mol), dissolved in 30 ml of dimethylsulphoxide, are added dropwise. After stirring has been carried out for 15 hours at 20° C., the suspension is poured onto 500 ml of water, the mixture is extracted with 600 ml of methylene chloride, the organic phase is extracted with 1 liter of water in each case, and the solvent is distilled off. The oily residue is taken up in 300 ml of diethyl ether, the other phase is filtered and the solvent is distilled off. 14 g (30.6% of theory) of 1-(4-chlorophenyl)-4-(dioxolan-2-yl)-2-(imidazol-1-yl)-4-methyl-pentan-3-one of refractive index $n_D^{20} = 1.5490$ are obtained.

Preparation of the starting material

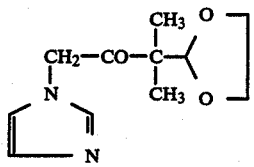

106.8 g (0.55 mol) of 1-chloro-3-(dioxolan-2-yl)-3-methyl-butan-2-one and 74.8 g (1.1 mols) of imidazole in 500 ml of acetonitrile are stirred for 15 hours at 65° C. The solvent is distilled off, the residue is taken up in 800 ml of methylene chloride and the solution is extracted with twice 1 liter of water. The methylene chloride phase is dried over sodium sulphate, and the solvent is distilled off. 71.7 g (57.7% of theory) of 1-(imidazol-1-yl)-3-(dioxolan-2-yl)-3-methyl-butan-2-one are obtained (purity according to gas chromatography 95.4%).

Example 7

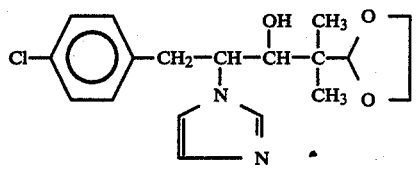

(Process c)

14.6 g (0.042 mol) of 4-(dioxolan-2-yl)-4-methyl-1-(4-chlorophenyl)-2-(imidazol-1-yl)-pentan-3-one are dissolved in 150 ml of methanol, and 2.065 g (0.055 mol) of sodium borohydride are added in portions at 0° C.; after a reaction time of 3 hours at room temperature, 15 ml of hydrochloric acid (concentrated) are added dropwise, and stirring is continued for a further 3 hours at room temperature, and 500 ml of saturated aqueous sodium bicarbonate solution are then added. The mixture is extracted with 400 ml of methylene chloride, the phases are separated, the organic phase is washed with twice 100 ml of water, and the solvent is distilled off. The residue is taken up in 150 ml of diisopropyl ether, and the solution is cooled to 0° C. 10.8 g (73.8% of theory) of 4-(dioxolan-2-yl)-4-methyl-1-(4-chlorophenyl)-2-(imidazol-1-yl)-pentan-3-ol of melting point 151°–157° C. crystallize out during this procedure.

The following compounds of the general formula

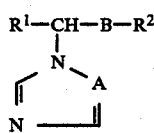

(I)

are obtained in an analogous manner and in accordance with the process variants given:

| Example No. | R¹ | R² | A | B | Melting point (°C.) or $n_D^{20}$ |
|---|---|---|---|---|---|
| 8 | 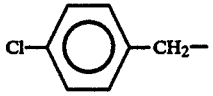 | —C(CH₃)₂—CH=CH₂ | N | CO | 43–48 |
| 9 | 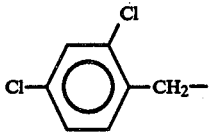 | —C(CH₃)₂—i-C₃H₇ | N | CO | 98–102 |
| 10 | 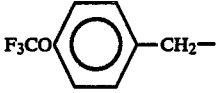 | —C(CH₃)₂—i-C₃H₇ | N | CO | 1.485 |
| 11 | 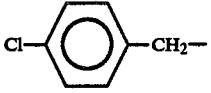 | 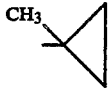 | N | CO | 60 |
| 12 | 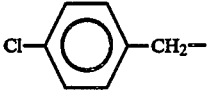 | —C(CH₃)₂—CH=CH₂ | N | CH(OH) | 132–46 |
| 13 | 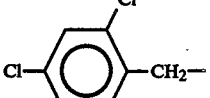 | —C(CH₃)₂—i-C₃H₇ | N | CH(OH) | 104–11 |
| 14 |  | —C(CH₃)₂—i-C₃H₇ | N | CH(OH) | 1.489 |
| 15 | CH₂=CH=CH₂— | —C(CH₃)₂—i-C₃H₇ | N | CH(OH) | 1.497 |
| 16 | CH₂=CH—CH₂CH₂— | —C(CH₃)₂—i-C₃H₇ | N | CH(OH) | 1.494 |
| 17 | 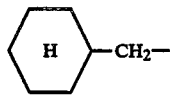 | —C(CH₃)₃₂—i-C₃H₇ | N | CH(OH) | 1.495 |
| 18 | n-C₄H₉— | —C(CH₃)₂—i-C₃H₇ | N | CH(OH) | 1.485 |
| 19 | 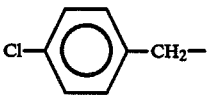 | 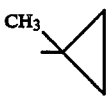 | N | CH(OH) | 118–20 (× HCl) |
| 20 | 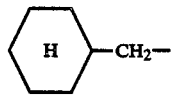 | 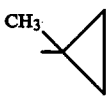 | N | CH(OH) | 160–66 (× HCl) |
| 21 | 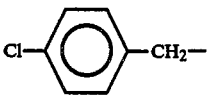 | 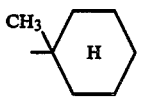 | N | CH(OH) | 170–72 (× HCl) |
| 22 | n-C₄H₉— | 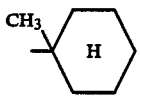 | N | CH(OH) | 156–60 (× HCl) |

-continued

| Example No. | R¹ | R² | A | B | Melting point (°C.) or $n_D^{20}$ |
|---|---|---|---|---|---|
| 23 | cyclohexyl-CH₂— (H) | 1-methylcyclohexyl (H) | N | CH(OH) | 125–27 (× HCl) |
| 24 | 2,4-dichlorophenyl-CH₂— | 1-methylcyclohexyl (H) | N | CH(OH) | 165 (× HCl) |
| 25 | 4-chlorophenyl-CH₂— | 1-methyl-4-isopropylcyclohexyl | N | CH(OH) | 130 |
| 26 | n-C₄H₉ | 1-methyl-4-isopropylcyclohexyl | N | CH(OH) | 94 (decomposition) |
| 27 | n-C₄H₉ | adamantyl | N | CH(OH) | 144–45 |
| 28 | 2,4-dichlorophenyl-CH₂— | —C(CH₃)₂—CH(1,3-dioxolan-2-yl) | CH | CO | 69–74 |
| 29 | 2,4-dichlorophenyl-CH₂— | —C(CH₃)₂—CH(1,3-dioxolan-2-yl) | CH | CH(OH) | 160–67 |
| 30 | 2,4-dichlorophenyl-CH₂— | 1-ethylcyclopentyl | N | CH(OH) | 138–45 (× HCl) |
| 31 | 4-fluorophenyl-CH₂— | —C(CH₃)₂—i-C₃H₇ | N | CH(OH) | 127–30 (× HCl) |
| 32 | 3,4-dichlorophenyl-CH₂— | —C(CH₃)₂—i-C₃H₇ | N | CH(OH) | 166–67 (× HCl) |
| 33 | n-C₄H₉ | —C(CH₃)₂—CH₂—C(CH₃)₃ | N | CH(OH) | 128–32 (× HCl) |
| 34 | n-C₄H₉ | —C(CH₃)₂—CH=CH₂ | N | CH(OH) | 137–38 (× HCl) |
| 35 | cyclohexyl-CH₂ (H) | —C(CH₃)₂—CH=CH₂ | N | CH(OH) | 156–58 (× HCl) |

-continued

| Example No. | R¹ | R² | A | B | Melting point (°C.) or $n_D^{20}$ |
|---|---|---|---|---|---|
| 36 | CF₃O-C₆H₄-CH₂- (para) | -C(CH₃)₂-CH=CH₂ | N | CH(OH) | 148-52 (× HCl) |
| 37 | CF₃O-C₆H₄-CH₂- (ortho) | -C(CH₃)₂-CH=CH₂ | N | CH(OH) | 168-72 (× HCl) |
| 38 | C₆H₁₁-CH₂- (cyclohexyl) | -C(CH₃)₂-n-C₃H₇ | N | CO | 1.4881 |
| 39 | (CH₃)₂CHCH₂CH₂- | -C(CH₃)₂-n-C₃H₇ | N | CO | viscous oil |
| 40 | n-C₄H₉ | -C(CH₃)₂-n-C₃H₇ | N | CO | 1.4748 |
| 41 | n-C₄H₉ | -C(CH₃)₂-n-C₃H₇ | N | CH(OH) | 1.4809 |
| 42 | Cl-C₆H₄-CH₂- (para) | -C(CH₃)₂-n-C₃H₇ | N | CO | 83 |
| 43 | 2,4-Cl₂-C₆H₃-CH₂- | -C(CH₃)₂-n-C₃H₇ | N | CO | 76 |
| 44 | C₆H₅-CH₂- | -C(CH₃)₂-n-C₃H₇ | N | CO | 1.5209 |
| 45 | (CH₃)₂CHCH₂CH₂ | -C(CH₃)₂-n-C₃H₇ | N | CH(OH) | 1.4789 |
| 46 | Cl-C₆H₄-CH₂- (para) | -C(CH₃)₂-n-C₃H₇ | N | CH(OH) | 106 |
| 47 | C₆H₁₁-CH₂- (cyclohexyl) | -C(CH₃)₂-n-C₃H₇ | N | CH(OH) | 1.4941 |
| 48 | C₆H₅-CH₂- | -C(CH₃)₂-n-C₃H₇ | N | CH(OH) | 1.5240 |
| 49 | 2,4-Cl₂-C₆H₃-CH₂- | -C(CH₃)₂-n-C₃H₇ | N | CH(OH) | 90-92 |
| 50 | n-C₆H₁₃ | -C(CH₃)₂-i-C₃H₇ | N | CH(OH) | 150 (× HCl) |
| 51 | 2,4-Cl₂-C₆H₃-CH₂- | -C(CH₃)₂-CH₂-C(CH₃)₃ | N | CH(OH) | 105-08 |

-continued

| Example No. | R¹ | R² | A | B | Melting point (°C.) or $n_D^{20}$ |
|---|---|---|---|---|---|
| 52 | 3,4-dichlorobenzyl (Cl, Cl–C₆H₃–CH₂–) | 1-methylcyclopropyl (CH₃, cyclopropyl) | N | CH(OH) | 168–74 (× HCl) |
| 53 | 4-(CF₃O)-benzyl | 1-methylcyclopropyl | N | CH(OH) | 148–50 (× HCl) |
| 54 | 4-(CF₃)-benzyl | 1-methylcyclopropyl | N | CH(OH) | 182–95 (× HCl) |
| 55 | 4-Cl-benzyl | –C(CH₃)₂–CH(OCH₃)₂ | N | CO | 1.5275 |
| 56 | 2,4-dichlorobenzyl | –C(CH₃)₃–CH(OCH₃)₂ | N | CO | 85–87 |
| 57 | 4-Cl-benzyl | –C(CH₃)₂–CH(OCH₃)₂ | N | CH(OH) | 1.5330 |
| 58 | 2,4-dichlorobenzyl | –C(CH₃)₂–CH(OCH₃)₂ | N | CH(OH) | 106–110 |
| 59 | 2,4-dichlorobenzyl | –C(CH₃)₂–CHO | N | CH(OH) | 141–44 |
| 60 | 4-Cl-benzyl | –C(CH₃)₂–CH(OCH₃)₂ | CH | CH(OH) | 154–60 |
| 61 | 2,4-dichlorobenzyl | –C(CH₃)₂–CH(OCH₃)₂ | CH | CH(OH) | 132–34 |
| 62 | 4-Cl-benzyl | –C(CH₃)₂–CH=NOCH₃ | N | CH(OH) | 175–77 (× HCl) |
| 63 | cyclohexyl-CH₂– | 1-methyl-4-isopropylcyclohexyl | N | CH(OH) | 74–76 |

-continued

| Example No. | R¹ | R² | A | B | Melting point (°C.) or $n_D^{20}$ |
|---|---|---|---|---|---|
| 64 | n-C₄H₉— | CH₃ (cyclopropyl with CH₃) | N | CH(OH) | 72–75 |
| 65 | cyclopentyl-CH₂— | —C(CH₃)₂—CH=CH₂ | N | CH(OH) | 144–48 (× HCl) |
| 66 | cycloheptyl-CH₂— | —C(CH₃)₂—CH=CH₂ | N | CH(OH) | 131–36 (× HCl) |
| 67 | 2-methylcyclohexyl-CH₂— | —C(CH₃)₂—CH=CH₂ | N | CH(OH) | 114–96 (× HCl) |

USE EXAMPLES

The compounds indicated below are employed as comparative substances in the examples which follow:

(A) 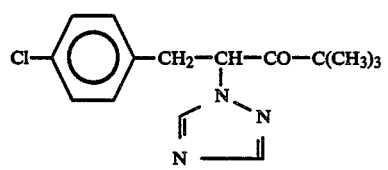

(B) 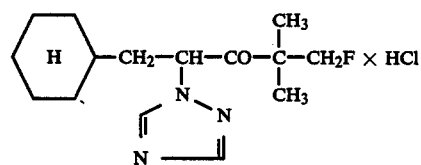

(C) 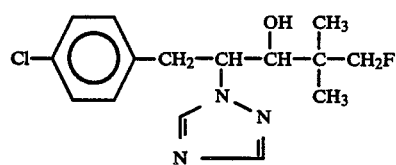

(D) 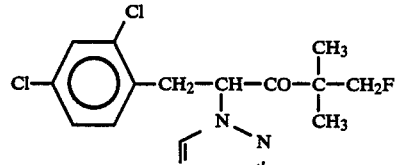

(E) 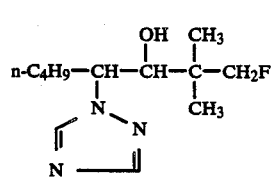

(F) 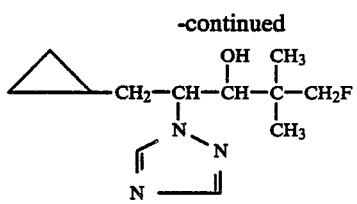

(G) 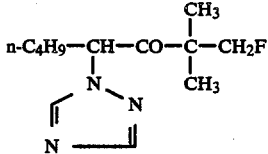

(H) 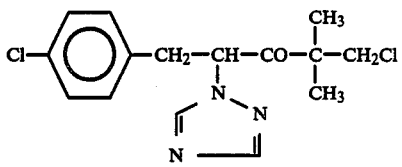

EXAMPLE A

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 2 and 13.

EXAMPLE B

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in the greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 11, 19, 8, 1, 9, 2, 13, 12, 21, 22, 23 and 24.

EXAMPLE C

Cochliobolus sativus test (barley)/protective
Solvent: 100 parts by weigh of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 2, 12, 21, 22, 23 and 24.

EXAMPLE D

Influence on growth of sugar beet
Solvent: 30 parts by weight of dimethylformamide
Emulsifier: 1 parts by weight of polyoxyethylene sorbitan monolaurate To produce a suitable preparation of active compound, 1 part by weight of active compound is mixed with the stated amounts of solvent and emulsifier and the mixture is made up to the desired concentration with water.

Sugar beet is grown in a greenhouse until formation of the cotyledons is complete. In this stage, the plants are sprayed with the preparation of active compound until dripping wet. After 14 days, the additional growth of the plants is measured and the influence on growth in percent of the additional growth of the control plants, is calculated. 0% influence on growth denotes a growth which corresponds to that of the control plants. Negative values characterize an inhibition of growth in comparison to the control plants, while positive values characterize a promotion of growth in comparison to the control plants.

In this test, the active compounds 8, 12, 1, 9, 13, 21, 22, 23 and 24 according to the invention have a better influence on growth than the compounds (B), (D), (E) and (F), which are known from the prior art.

EXAMPLE E

Inhibition of growth of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 3 weeks, the additional growth of the plants is measured and the inhibition of growth in percent of the additional growth of the control is calculated. 100% inhibition of growth means that growth has stopped and 0% denotes a growth corresponding to that of the control plants.

In this test, the active compounds 8, 12, 2, 13, 21, 22, 23 and 24 according to the invention effect better inhibition of growth than the compounds (B), (D), (E), (F), (G) and (H), which are known from the prior art.

EXAMPLE F

Inhibition of growth of soy beans
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. In this stage, the plants are sprayed with the preparations of active compound until dripping wet. After 3 weeks, the additional growth is measured on all the plants and the inhibition of growth in percent of the additional growth of the control plants is calculated. 100% inhibition of growth means that growth has stopped and 0% denotes a growth corresponding to that of the control plants.

In this test, the active compound 8, 12, 1, 2, 13, 21, 22, 23 and 24 according to the invention effect better inhibition of growth than the compounds (B), (D), (E), (F) and (G), which are known from the prior art.

EXAMPLE G

Stimulation of the fixation of $CO_2$ in soy beans
Solvent: 30 parts by weight of dimethylformamide Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. At this stage, the plants are sprayed with the preparations of active compound until dripping wet. In the further course of the experiment, the fixation of $CO_2$ in the plants is determined by customary methods. The values are compared with those of the control plants, which have not been treated with the active compounds.

In this test, the active compounds 20, 1 and 13 according to the invention effect better stimulation of the fixation of $CO_2$ than the compounds (C), (D), (E), (G) and (H), which are known from the prior art.

It will be appreciated that the instant specification and examples are set forth by way of illustration and not limitation, and that various modifications and changes may be made without departing from the spirit and scope of the present invention.

We claim:

1. A substituted azolyl ketone or -alcohol of the formula

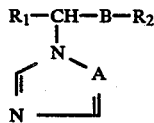

in which

B is CO or CH (OH), $R_1$ is benzyl optionally mono- or di- substituted by chlorine, $R_2$ is cycloalkyl with 3–7 carbon atoms which is mono-, di- or trisubstituted with alkyl radicals with 1–4 carbon atoms, or an addition product thereof with an acid or metal salt.

2. A compound according to claim 1, wherein such compound is 1-(4-chlorophenyl)-3-(1-methyl-cyclohexyl)-2-(1,2,4-triazol-1-yl)-propan-3-ol of the formula

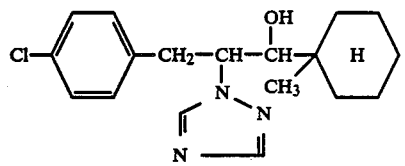

or an addition product thereof with an acid or metal salt.

3. A compound according to claim 1, wherein such compound is
3-(4-chlorophenyl)-1-(1-methyl-cyclopropyl)-2-(1,2,4-triazol-1-yl)-propan-1-one of the formula

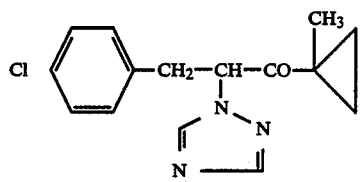

or an addition product thereof with an acid or metal salt.

4. A fungicidal or plant growth regulating composition of matter comprising a fungicidally or plant growth regulating effective amount of a compound or addition product according to claim 1 in admixture with a diluent.

5. A method of combating fungi which comprises administering to such fungi or to a fungus habitat a fungicidally effective amount of a compound or addition product according to claim 1.

6. A method of combating fungi according to claim 5 where such compound is
1-(4-chlorophenyl)-3-(1-methyl-cyclohexyl)-2-(1,2,4-triazol-11-yl)-propan-3-ol,
3-(4-chlorophenyl)-1-(1-methyl-cyclopropyl)-2-(1,2,4-triazol-1-yl)-propan-1-one,
1-(1-methyl-cyclohexyl)-2-(1,2,4-triazol-1-yl)-n-hexan-1-ol,
or an addition product thereof with an acid or metal salt.

7. A method of regulating the growth of plants which comprises applying to such plants or to a plant habitat a plant growth regulating effective amount of a compound or addition product according to claim 1.

8. A method or regulating the growth of plants according to claim 7, wherein such compound is
1-(4-chlorophenyl)-3-(1-methyl-cyclohexyl)-2-(1,2,4-triazol-1-yl)-propan-3-ol,
3-(4-chlorophenyl)-1-(1-methyl-cyclopropyl)-2-(1,2,4-triazol-1-yl)-propan-1-one,
1-(1-methyl-cyclohexyl)-2-(1,2,4-triazol-1-yl)-n-hexan-1-ol,
or an addition product thereof with an acid or metal salt.

* * * * *